United States Patent [19]

Juge et al.

[11] Patent Number: 4,694,094

[45] Date of Patent: Sep. 15, 1987

[54] CYCLIC DIPHOSPHONITES

[75] Inventors: Sylvain Juge, Puteaux; Yvonne Legras, Paris, both of France

[73] Assignee: Societe Nationale Elf Aquitaine, France

[21] Appl. No.: 736,447

[22] Filed: May 21, 1985

[30] Foreign Application Priority Data

May 25, 1984 [FR] France ................................ 84 08215

[51] Int. Cl.⁴ .............................................. C07F 9/15
[52] U.S. Cl. ......................................... 558/76; 558/78
[58] Field of Search .............................. 558/76, 77, 78

[56] References Cited

FOREIGN PATENT DOCUMENTS 2159158 11/1985 United Kingdom .................. 558/78

*Primary Examiner*—Anton H. Sutto
*Attorney, Agent, or Firm*—Ostrolenk, Faber, Gerb & Soffen

[57] ABSTRACT

New organic compounds containing a phosphorus heterocycle of the phosphonite type, in which the phosphorus atom is connected on the one hand to an oxygen atom and on the other hand to an oxygen, sulphur or nitrogen atom, characterized by comprising two of such heterocycles, the two phosphorus atoms being connected by a hydrocarbon group. Preparation of these diphosphonites by the action of a tetrahalogeno- or tetraminodiphosphine upon a diol or an alcohol carrying a phenol, thiol, enol, acid or amine function.

5 Claims, No Drawings

CYCLIC DIPHOSPHONITES

The invention relates to a new class of cyclic phosphonites, particularly the diphosphonites and their derivatives, in which one of the oxygen atoms connected to a phosphorus is replaced by an atom of sulphur or nitrogen. It also comprises a process of preparation of such compounds, as well as their uses.

The phosphonites, particularly the optically-active compounds, have industrial utility both as such and as starting materials for the preparation of other useful products, particularly phosphinates, phosphine oxides, phosphinamides etc. Various natural and synthetic products can be prepared at present by asymmetric synthesis, catalyzed by means of transition metals and particularly with catalysts comprising optically-active organo-phosphorus ligands. Thus, substances of interest in agriculture, food, pharmacy and perfumery are so prepared. The production of L-dopa, so useful in therapeutics, in particular for the treatment of Parkinson's disease, is an example. The new cyclic diphosphonites according to the invention are suitable as transition metal ligands; this complexing property permits their use in the selective extraction of metals or the formation of complex metal catalysts. These diphosphonites can also serve as additives for plastics materials, in particular for stabilization and flame-retardancy. Pesticides based on these compounds can be utilized. When the part of the ring connected to the phosphorus includes an antibiotic molecule, the diphosphonite has improved biocidal properties; this is so, for example, where this part of the ring is derived from chloramphenicol. Complexes with noble metals can serve by reason of their antiviral or antitumoral properties.

Use of the new diphosphonites in the preparation of the corresponding phosphinates takes place easily through the action of an alkylating agent, for example an aliphatic or aryl halide; the asymmetry of the diphosphonite permits locally selective opening of the heterocycles by this reaction.

The present invention relates to cyclic phosphonites similar to those of the prior art, namely the dioxa-, oxathia- and oxaza-phospholanes, phosphorinanes or phosphonanes, but characterized by comprising two phosphorus-containing rings, the two P atoms being connected by a hydrocarbon group.

It appears that the double presence of the phosphorus-containing ring provides the molecule with interesting properties, generally increasing its activity in the various uses of the compound.

The new products according to the invention can be represented by the general formula:

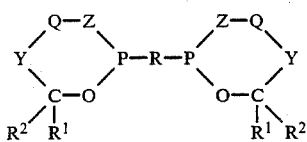

(1)

where Z designates O, S or NH, where the H can be replaced by a hydrocarbon group, substituted if required; $R^1$ and $R^2$ are the same or different and are alkyls or alkenyls, preferably from $C_1$ to $C_{18}$, cycloalkyls or even aryls, the substituents preferably being such as halogens, nitro, nitriles, amide, ester, ether, acetal or lactone; or alternatively $R^1$ and/or $R^2$ can be H atoms.

R is a divalent hydrocarbon group, more particularly aliphatic, saturated or unsaturated, and preferably from $C_1$ to $C_6$; thus R can be a chain $-(CH_2)_n-$ where $n=1$ to 6, branched if required, or such a chain comprising double bonds, particularly $-CH_2-CH=CH-CH_2-$,

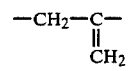

or the like.

Y can comprise a simple bond between $-C-R^1$ and Q, in which case the ring has five elements, but Y preferably forms an aliphatic chain or an aliphatic or aryl ring, providing 2 to 5 elements of the oxyphosphorus ring, which therefore comprises 6 to 9 elements. When Y is a chain or a ring, for example:

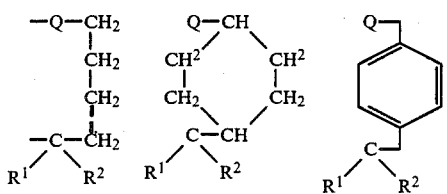

all or part of the H atoms can be replaced by aliphatic or aryl radicals and/or by functional groups, particularly such as those mentioned above in relation to $R^1$ and $R^2$.

Q represents a group which can be of the same type as the lower part of the formula (1), namely:

$R^3$ and $R^4$ corresponding to the same definition as $R^1$ and $R^2$, but they can be different from the latter.

Another form of Q is an aliphatic or aryl ring on which various substituents are carried, in particular those indicated further above. Such a ring can also form part of a metallocene.

According to a variant, Q itself comprises a metallocene, for example ferrocenyl, chromocenyl or the like. Also, if required it can form a group

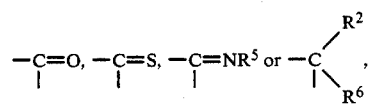

where $R^5$ and $R^6$ are defined like the radicals $R^1$, $R^2$ above.

It will be understood that, depending upon the nature of Z in the new compounds according to the invention, the nomenclature changes: when Z is a sulphur atom, the compound is a di(oxa-thia-phospholane) and, if Z is a

or an

the product is a di(oxazaphospholidine). However, for simplification, mention will continue to be made in the present description of cyclic diphosphonites as regards all the compounds corresponding to the formula (1).

By way of example, the formula of one of the most simple compounds according to the invention is:

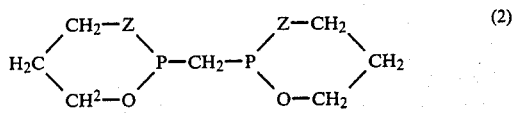

However, for different uses, the heavier compounds containing various substituents for H in formula (2) are suitable in general. On the other hand, the phosphorus-containing heterocycle can comprise 5 to 9 elements in place of the six elements of this formula (2).

When an optically-active compound is concerned, it is recommendable to use a compound derived from a diphosphonite, according to the invention, having considerable asymmetry. It is useful to employ compounds according to formula (1) in which a plane perpendicular to the page of this formula, passing through the two P atoms, divides the molecule into two parts of different molecular weights. In other words, the —Z—Q groups, if required, with a part of Y, thus have a molecular weight different from that of the groups

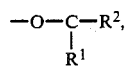

if required with a part of Y; preferably the ratio between these two molecular weights is at least 1.5. Particularly active products have a ratio from 2 to 10.

The new diphosphonite compounds according to the invention have the advantage that their conversion into other derivatives gives the latter in a state of considerable diastereo-isomeric purity, when the starting material for the preparation of the diphosphonic heterocycles is optically pure. This permits the production in particular of diphosphonites of excellent diastereoisomeric purity, by the locally selective opening of the diphosphonite rings and their use for the preparation of diphosphine oxides or diphosphinamides.

An advantageous process of preparation of the new compounds according to the invention consists in reacting one mole of a tetrahalogeno- or tetraminodiphosphine,

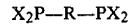

where X is a halogen or an amino group, with 2 moles of an organic compound carrying at least 2 groups having H atoms capable of reacting with the halogens or the amino groups of the diphosphine. This compound can be represented by the formula:

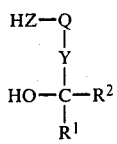

where the symbols Z, Q, Y, $R^1$ and $R^2$ have the same significance as above.

As can be seen, the at least di-functional compound (3) can be a diol, alcohol-phenol, alcohol-thiol, alcohol-enol, alcohol-acid or amino acid, in view of the various possible functions of ZH. The two functions, OH and ZH, can be located in different respective positions, but more especially alpha, beta, gamma, delta or epsilon with respect to one another. Designated here generically by the term diphosphonites, these compounds are in fact bis dioxa-, oxathia- or oxaza-1,3,2-phospholanes, phosphorinanes or phosphonanes.

The reaction of a tetrahalogeno-diphosphine, for example a tetrachloroalkane or aryl diphosphine, $Cl_2P$—R—$PCl_2$, with a compound of the formula (3) produces 4 HCl per mole of diphosphine; this acid is eliminated by a neutralizing agent or by a suitable base added to the reaction medium; this generally comprises a solvent for the reacting materials. Preferably, the neutralizing agent and the solvent are selected in such a way that the halide, particularly the chloride, formed will precipitate. Neutralizaion can take place with the aid of amines, particularly tertiary, notably pyridine, triethylamine, tributylamine, etc., being suitable, in particular with tetrahydrofuran or toluene as the solvent, in which their hydrochlorides are insoluble. According to a feature of the invention, the base is employed in an excess of 3% to 12% with respect to its stoichiometric quantity required.

Although the reaction can be carried out at temperatures from about $-5°$ to $+25°$ C., according to a preferred feature of the invention, operation occurs between $-3°$ and $+5°$ C. and particularly between $-2°$ and $+4°$ C.

According to a variant of the invention, the reaction of one equivalent of tetramino-diphosphine with two equivalents of the compound of formula (3) produces 4 $HNR_2'$ per mole of diphosphine. When R' is a radical of a relatively low molecular weight, for example a lower alkyl ($C_1$ to $C_4$), the base $HNR_2'$ can be eliminated from the reaction medium by sweeping with a neutral gas, preferably nitrogen or argon.

In this preparation, aprotic solvents are particularly suitable, particularly aromatics, such as benzene or toluene.

The reaction of the above variant is illustrated by the following equation, in the simple case where —Q—Y—$CR^1R^2$ of the formula (3) is —$CH_2CH_2$—, Z being an —NR":

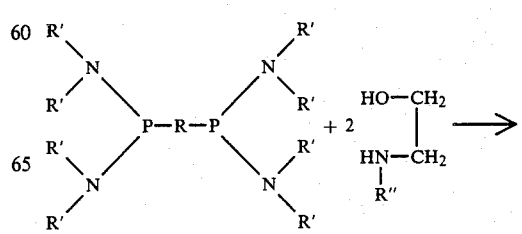

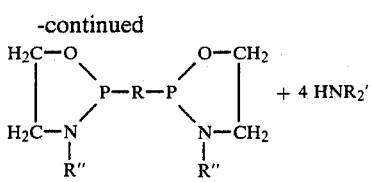

substituted bis-oxazaphospholidine.

This reaction can be effected at a temperature ranging from 50° to 160° C., but preferably between 90° and 120° C.; the preferred temperatures are between 105° and 115°, thus as close as possible to 110° C., when R' is a $C_1$ to $C_4$ alkyl.

The invention is illustrated non-limitatively by the following examples. The compounds, preparation of which is described in these examples, are all new chemical products, none having been described, to the knowledge of the inventors, in prior chemical literature.

EXAMPLE 1

Preparation of (−)
1,2-bis[5-dichloroacetamido-4(4-nitrophenyl)-1,3,2-dioxaphosphorinane-2-yl(2R,4R,5R)]-ethane

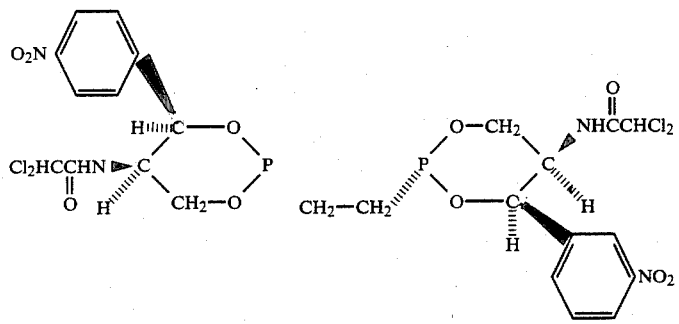

This is the compund of formula (1) in which Z is oxygen, $R^1$ is H, $R^2$ is nitrophenyl, Q is $CH_2$ and Y is

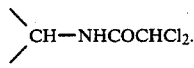

It is obtained by the reaction of 2 moles of chloramphenicol with 1 mole of tetrachloro-1,2-diphosphinoethane, in the presence of 4.2 moles of triethylamine:

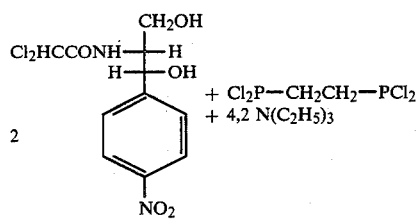

For this, 14.1 g of chloramphenicol of 98.8% purity is dissolved with 5 g of tetrachloro-1,2-diphosphinoethane in 500 ml of dry tetrahydrofuran (THF) at 0° C. under argon atmosphere. To the solution obtained, 9.2 g of triethylamine is added and the mixture is agitated for one hour, the medium being maintained at 0° C.

The precipitate of triethylamine hydrochloride is then eliminated by filtration; subsequent evaporation of the solvent leaves 15.5 g of product in the form of a spongy mass which comprises the bis-dioxa-phosphorinane of formula (4), obtained in a yield of 98%.

Characteristics of this compound: Pasty fusion at about 120° C.

NMR $^{31}P$ (THF+Toluene $D_8$)+165.8 ppm.

| Analysis: | C % | H % | N % |
|---|---|---|---|
| Calculated | 39.40 | 3.30 | 7.65 |
| Found | 39.48 | 3.76 | 7.26 |

$[\alpha]_D^{20} = -64.8$ c=4(THF).

EXAMPLE 2

Preparation of
1,2-bis[1,3,2-dioxaphospholane-2-yl]-ethane 2.32 g (0.01 mole) of tetrachloro-1,2-diphosphinoethane is dissolved with 1.22 g of ethylene glycol (0.02 mole) in 200 ml of THF at 0° C. under an argon atmosphere. 4.2 equivalents of triethylamine (4.24 g) are then added. After agitation for 1 hour, the hydrochloride (4)

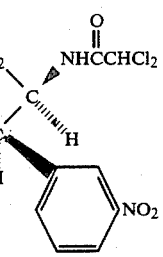

precipitate is filtered off and the solvent is evaporated, which allows recovery of 2 g of a colourless oil which is distilled. Yield 95%.

Eb: 110°/0.4 mbar

| NMR $^1H$ (toluene D8) | | |
|---|---|---|
| 1.4 ppm | multiplet | (4H) |
| 3.4 ppm | " | (8H) |

NMR$^{31}$P: +178 ppm.

| analysis: $C_6H_{12}O_4P_2$ | | M = 210 | |
|---|---|---|---|
| | C | H | O | P |
| Calculated % | 34.3 | 5.7 | 30.5 | 29.5 |
| Found % | 33.9 | 5.7 | 30.9 | 29.4 |

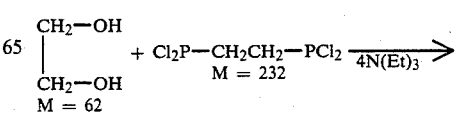

-continued

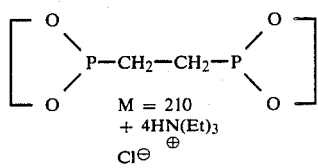
M = 210
+ 4HN(Et)$_3$
Cl$^\ominus$

EXAMPLE 3

Preparation of 1,2-bis[4,4,5-trimethyl-1,3,2-dioxaphospholane-2-yl(2R,5S)]-ethane

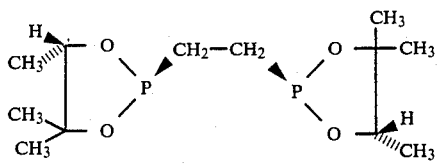

According to an operative mode similar to that of Example 2, 2.32 g (0.01 mole) of tetrachloro-1,2-diphosphinoethane is dissolved in 200 ml of THF with 2.04 g of (+) 2-methyl-2,3-butanediol prepared from (−) ethyl lactate [JCS Perkin I 2114 (1974)].

4.24 g of triethylamine is then added. After agitation for 1 hour, the precipitate of hydrochloride is filtered off and the solvent is evaporated which allows recovery of 2.9 g of a colourless oil (yield 98%) which is distilled.

Eb=130°/0.066 mbar

NMR$^1$H (toluene D8): multiplet 0.9–1.3 ppm (18H), quadruplet 3.55 ppm (2H).

NMR$^{31}$P (toluene D8)+177 ppm.

| analysis: C$_{12}$H$_{44}$O$_4$P$_2$ | M = 294 | | | |
|---|---|---|---|---|
| | C | H | O | P |
| Calculated = % | 50 | 8.2 | 21.8 | 21.1 |
| Found = % | 48.6 | 8.1 | 22.2 | 21 |

EXAMPLE 4

Preparation of 1,2-bis[4,4-diphenyl-5-methyl-1,3,2-dioxaphospholane-2-yl(2R,5S)]-ethane

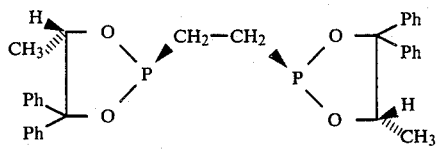

According to an operative mode identical to that of Example 3, this compound is obtained from 4.46 g of (−) 1,1-diphenyl-1,2-propanediol previously prepared from (−) ethyl lactate [Tetrahedron 507(1977)]. 5.1 g of a thick oil is obtained.

(Yield: 94%).

NMR $^1$H (toluene D8): doublet (6H) 1.05 ppm, multiplet (4H) 2.1 ppm, quadruplet (2H) 4.8 ppm, massive (20H) 7–7.7 ppm.

NMR $^{31}$P (toluene D8)+180 ppm

| analysis: C$_{32}$H$_{32}$O$_4$P$_2$ | M = 542 | | | |
|---|---|---|---|---|
| | C | H | O | P |
| Calculated = % | 70.8 | 5.9 | 11.8 | 11.4 |
| Found = % | 70.4 | 5.9 | 12.2 | 11.2 |

EXAMPLE 5

Preparation of 1,2-bis[3,4-dimethyl-5-phenyl-1,3,2-oxazaphospholidine-2-yl(2R,4S,5R)]-ethane

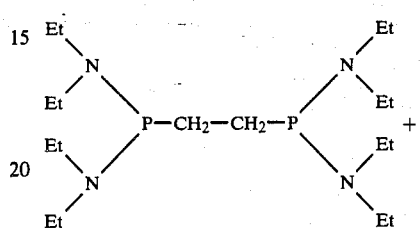
+

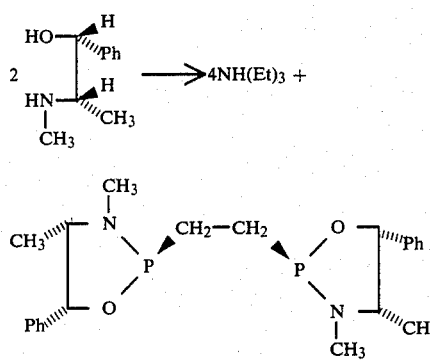

The preparation is effected in a three-necked 1 liter flask equipped with an agitator and 2 nozzles for the introduction and removal of the nitrogen purge. In this way, the amine liberated during the reaction is entrained from the medium and can be measured in a washing flask. 0.02 mole of (−) ephedrine is reacted with 0.01 mole of 1,2-bis[tetraethyl-diaminophosphino]-ethane for 12 hours in 200 ml of toluene between 100° and 110° under a light nitrogen purge. At the end of this time, the reaction medium is transferred to an evaporation flask and the solvent is evaporated. 4.2 g of a thick oil (yield 100%) is obtained, which is taken as such to the refrigerator and has the following characteristics:

| NMR$^1$H (toluene D8) | | |
|---|---|---|
| 0.5 ppm doublet | J = 7 Hz | 6 H |
| 2.1 ppm multiplet | | 4 H |
| 2.25 ppm doublet | | 6 H |
| 3.1 ppm multiplet | | 2 H |
| 5.3 ppm doublet | J = 7 Hz | 2 H |
| 7.25 ppm multiplet | | 10 H |

NMR $^{31}$P (toluene D8)+155 ppm

| analysis: C$_{22}$H$_{30}$N$_2$O$_2$P$_2$ | M = 416 | | | | |
|---|---|---|---|---|---|
| | C | H | N | O | P |
| Calculated: % | 63.5 | 7.2 | 6.7 | 7.7 | 14.9 |
| Found: % | 63 | 7.3 | 6.8 | 8 | 14.7 |

EXAMPLE 6

Use of the diphosphonite derived from chloramphenicol (Example 1) in the preparation of 1,2-diphosphinato-ethane (di-phosphinate)

Compound according to formula 4 (Example 1)

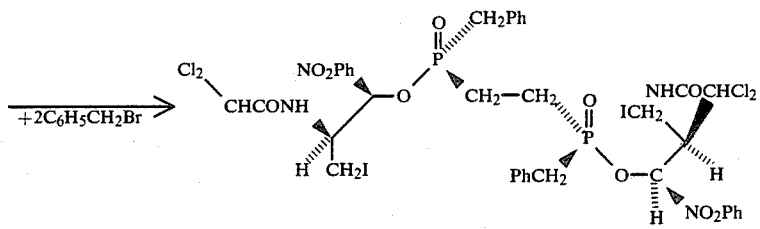

6.6 g of the diphosphonite prepared in Example 1 and 30 ml of benzyl bromide are reacted at 100° C. under nitrogen for 24 hours.

The excess halide is then evaporated under vacuum. The product obtained (9.2 g) has the following characteristics:

Non-crystalline solid: pasty fusion 100°–120°
NMR $^{31}P = +57.07$ ppm $CD_3OD$ Uses similar to that of Example 6 can be carried out by replacing the alkyl or aryl halide with other alkylating agents such as the alkene halides, particularly 1,2-chloroethane, halides of dichloroisocyanate acids, chloroimides, alkyl sulphates, alkyl tosylates, lactones, nitrated compounds, particularly nitro-olefins, or others.

The diphosphinate so obtained can be converted to another, particularly into a simpler diphosphinate, by the action of an alkali metal alcoholate according to the reaction

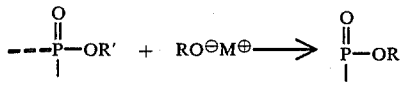

where R is for example $CH_3$ or $C_2H_5$ and M is Na or K. Use of the diphosphinate according to the invention thus comprises two stages: treatment by an alkylating agent, followed by an alkali metal alcoholate.

Another use is the preparation of diphosphine oxides, which can be obtained by the reaction of a diphosphinate with an organo-metallic halide. This applies both to the diphosphonites per se and to their thio-derivatives, in which one of the oxygen atoms connected to th phosphorus atom is replaced by an S.

When the starting diphosphonite carries a nitrogen atom in place of one of the oxygens and thus produces a diphosphinamide under the action of an alkylating agent, a diphosphinate can thus be obtained by reacting this diphosphinamide with an alcohol in an acid medium according to the scheme:

We claim:

1. Compound of the formula

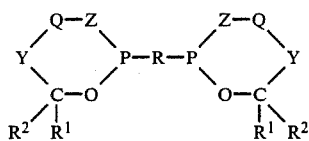

where Z is O or $NR^7$ in which $R^7$ is H or $CH_3$; $R^1$ and $R^2$ are independently selected from the group consisting of H, methyl, phenyl and nitrophenyl; R is $-CH_2CH_2-$; Y represents a bond or $>CHNHCOCHCl_2$ and Q is $-CH_2-$ or $>CHCH_3$.

2. The compound according to claim 1 which is asymmetric.

3. The compound according to claim 1 in which $R^7$ is $CH_3$.

4. The compound according to claim 1 which is selected from the group consisting of 1,2-bis[5-dichloroacetamido-4(4-nitrophenyl)-1,3,2-dioxaphosphorinane-2-yl]ethane; 1,2-bis[1,3,2-dioxaphospholane-2-yl]ethane; 1,2-bis[4,4,5-trimethyl-1,3,2-dioxaphospholane-2-yl]ethane; 1,2-bis[4,4-diphenyl-5-methyl-1,3,2-dioxaphospholane-2-yl]ethane; and 1,2-bis[3,4-dimethyl-5-phenyl-1,3,2-oxazaphospholidine-2-yl]ethane.

5. Compound of the formula.

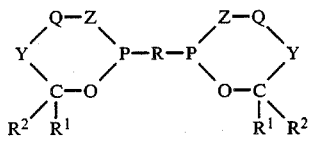

where Z is O or $NR^7$ in which $R^7$ is H or $CH_3$; $R^1$ and $R^2$ are independently selected from the group consisting of H, methyl, phenyl and nitrophenyl; R is $-CH_2CH_2-$; Y represents a bond or $>CHNHCOCHCl_2$ and Q is $>CR_1R_2$.

* * * * *